United States Patent [19]

Mets

[11] Patent Number: 5,240,842
[45] Date of Patent: Aug. 31, 1993

[54] AEROSOL BEAM MICROINJECTOR

[75] Inventor: Laurens J. Mets, Chicago, Ill.

[73] Assignee: Biotechnology Research and Development Corporation, Peoria, Ill.

[21] Appl. No.: 902,478

[22] Filed: Jun. 19, 1992

Related U.S. Application Data

[63] Continuation of Ser. No. 378,256, Jul. 11, 1989, abandoned.

[51] Int. Cl.$^5$ ............... C12N 15/87; C12N 15/89; C12N 15/90
[52] U.S. Cl. ............... 435/172.3; 435/172.1; 935/52; 935/53; 935/85
[58] Field of Search ............... 435/172.1, 172.3; 935/52, 53, 85

[56] References Cited

U.S. PATENT DOCUMENTS 4,945,050  7/1990  Sanford et al. ............... 435/172.1
5,141,131  8/1992  Miller et al. ............... 222/54

FOREIGN PATENT DOCUMENTS 0270356  2/1987  European Pat. Off. .

OTHER PUBLICATIONS

Wastie 1984 Plant Pathology 33: 61–63.
Moynahan et al 1965 British Medical Journal 3: 1541–1543.
Lachapelle et al, 1982 Ann Dermatol. Venereol. (Paris) 109: 939–946.
Sanford, John C. et al., Delivery of substances into cells and tissues using a particle bombardment process. Particulate Science and Technology 5:27–37, 1987.
Johnston, Stephen A. et al., Mitochondrial Transformation in Yeast by Bombardment with Microprojectiles. Science, vol. 240 pp. 1538–1540.
Sanford, John C., The Biolistic process. Tibtech—Dec. 1988 vol. 6, pp. 299–302.
Sanford, John, The Biolistic Process. Amer. Soc. Plant Physiologists Aug. 1989, pp. 2.
Christou, Paul et al., Soybean transformation using electric discharge particle acceleration. Amer. Soc. Plant Physiologists Aug. 1989 pp. 2.
Boynton, John E. et al., Chloroplast Transformation in Chlamydomonas with High Velocity Microprojectiles.- Science, vol. 240 pp. 1534–1537.
Klein, T. N., et al., High–velocity microprojectiles for delivering nucleic acids into living cells. Nature vol. 327 May 1987, pp. 70–73.

(List continued on next page.)

*Primary Examiner*—Elizabeth C. Weimar
*Assistant Examiner*—P. Moody
*Attorney, Agent, or Firm*—Foley & Lardner

[57] ABSTRACT

The present invention uses aerosol beam technology to accelerate either wet or dry aerosol particles to speeds enabling the particles to penetrate living cells. Aerosol particles suspended in an inert gas are accelerated to a very high velocity during the jet expansion of the gas as it passes from a region of higher gas pressure to a region of lower gas pressure through a small orifice. The accelerated particles are positioned to impact a preferred target, for example, a plant or animal cell or bacterial culture. When the droplets include DNA or other macromolecules, the macromolecules are introduced into the cells. The particles are constructed as droplets of a sufficiently small size so that the cells survive the penetration. Once introduced into the target cell the macromolecules can elicit biological effects. Because the method of introduction is a physical one, the biological barriers that restrict the application of other DNA transfer methods to a few plant species and a few cell types are not present. In addition, the method and apparatus of the present invention permit the treatment of a large number of cells in the course of any single treatment. Thus, the inventive method and apparatus should be applicable to a wide range of plant species and cell types that have proved in the past to be quite impervious to standard methods of genetic engineering.

8 Claims, 3 Drawing Sheets

OTHER PUBLICATIONS

Wang, Yi-Chang et al., Transient expresson of foreign genes in rice, wheat and soybean cells following particle bombardment. Plant Molecular Biology 11:433–439.

Klein, Theodore M. et al., Stable genetic transformation of intact Nicotiana cells by the particle bombardment process. Proc. Natl. Acad. Sci. USA vol. 85, pp. 8502–8505, Nov. 1988.

Christou, Paul et al., Stable Transformation of Soybean Callus by DNA-Coated Gold Particles. Plant Physiol, 1988, 87, 671–674.

Bryant, John A. Putting genes into plants. Plants today Jan.-Feb. 1988/23.

Lee, Bruce, Cereal transformation. Plants Today Jan.-Feb. 1989/9.

Chupeau, Marie-Christine, et al., Transgenic Plants of Lettuce (*Lactuca sativa*) Obtained through Electroporation of Protoplasts. Bio/Technology vol. 7 May 1989, pp. 503–508.

Chassy, Bruce M., et al., Tansformation of bacteria by electroporation. Tibtech—Dec. 1988 vol. 6, pp. 303–309.

Bio Rad. Gene Pulser Electroporation Apparatus, Bulletin 1272.

Dahneke, B. E., et al., Properties of Continuum Source Particle Beams. I. Calculation Methods and Results. J. Aerosol Sci. vol 10, pp. 257–274.

Dahneke, Barton, et al., Prog. Astronautics & Aeronautics 74:504–514 (1981), pp. 504–514.

Israel, Gerhard, et al., High-Speed Beams of Small Particles. Journal of Colloid and Interface Science 24, 330–337, 1967.

Mora de la, Fernandez J., Surface impact of seeded jets at relatively large background densities. Yale University 1984.

Dahneke, Barton, et al., An Aerosol Beam Spectrometer. Aerosol Science, 1972 vol. 3, pp. 345–349.

Mayer, Erwin, New method for vitrifying water and other liquids by rapid cooling of their aerosols. American Inst. of Physics. Jul. 1985, pp. 663–667.

AEROSOL BEAM MICROINJECTOR

This is a continuation of application Ser. No. 07/378,256 filed Jul. 11, 1989, now abandoned.

BACKGROUND OF THE INVENTION

The present invention relates to the introduction of exogenous material into a living cell, tissue, or species, and more particularly, to apparatus and methods for microinjecting exogenous materials into a living cell, tissue, or species.

DESCRIPTION OF THE PRIOR ART

The genetic transformation of cells using the techniques of genetic engineering has grown dramatically over the last few years. Generally, genetic engineering involves the introduction of foreign DNA into a host cell to change or "transform" the host cell. When successfully done, the genes carried by the foreign DNA are expressed in the host cell, and thus, the host cell is transformed.

Genetically transformed cells, tissues, or species are of great commercial value in research, agriculture, and medicine. For example, human insulin is presently being produced by bacteria which have been genetically engineered. Human insulin is now available in commercial quantities, and has benefitted millions of diabetics throughout the world. In addition, several plant species have been genetically engineered to produce more crop, become more resistant to disease, and grow in less hospitable climates and soils.

Because of the commercial and social importance of genetic engineering, a plurality of methods for transferring foreign genes into a recipient cell have been developed for both procaryotic and eucaryotic cells. These gene transfer techniques are routinely used in laboratories throughout the world to genetically transform living cells, tissues and species. However, despite the existence of these diverse transformation techniques, the effective stable transfer of genes remains an obstacle in many fields of research. One technique for gene transfer is cell fusion. Cell fusion has been applied to both animal and plant cell cultures. Cell fusion techniques integrate the genetic information of two different cells in one. In plant cell cultures, cell walls are dissolved and the naked protoplasts are fused together, forming a new cell. The descendants of the new fused cell express certain characteristics of both the original (parent) cells. However, researchers have no means of predicting what characteristics will be expressed in the progeny. Thus, the results obtained using cell fusion techniques are unpredictable and are generally not reproducible.

In animal cell cultures, hybridomas are the cell fusion product of antibody-secreting cells and "immortal" cells (myelomas). Hybridomas are used in medicine and research to produce monoclonal antibodies. Hybridomas, like the plant cell fusion products, may react unpredictably, and are expensive to produce and maintain.

Electroporation is another general method for introducing foreign DNA into cells. This procedure involves the exposure of a suspension of cells and fragments of foreign DNA to a pulsed high-voltage electrical discharge. This electrical discharge creates holes or pores in the cell membrane through which DNA fragments diffuse. Upon cessation of the electrical discharge, the pores in the cell membrane close, capturing any DNA fragments which have diffused into the cell. However, a major drawback in using electroporation to introduce DNA into living cells is the necessity prior to a successful transformation, to determine empirically optimum values for a wide variety of parameters for each cell line in question. These parameters include voltage, capacitance, pulse time composition and resistance of electroporation medium, state of cell growth prior to electroporation, concentration of DNA, temperature, and cell density. Also, present methods for applying electroporation to cells with walls, such as plant cells, require removing the walls prior to electroporation. These protoplasts must then regenerate their walls before they can divide and be regenerated into intact plants. Since not many plants can yet be regenerated from protoplasts, this requirement limits applicability of electroporation.

Viral infection is also an efficient means of transferring foreign DNA into some cells. However, viruses are difficult to work with, and since a particular virus will only infect certain cells, the technique is not applicable to the broad spectrum of living cells, tissue, or species. Further, some virus may in fact be hazardous to the technicians working with them or to the environment.

The most common and effective method for transferring genes into plant cells involves conjugal transfer from living bacteria, primarily *Agrobacterium tumefaciens* and *Agrobacterium rhizogenes*. The DNA to be transferred is first engineered into plasmids derived from the bacterial Ti plasmid, and the bacteria are then incubated in culture with the recipient plant cells. The cultured, transformed cells must then be regenerated into genetically homogeneous plants. This method is limited to plants susceptible to Agrobacterium infection (principally dicots) that can be regenerated from cultures.

Still another technique for gene transfer is micropipette microinjection. In micropipette microinjection, DNA or other exogenous materials, are stably introduced into a living cell by microinjecting the material directing into the nuclei of the cell. Typically, a glass micropipette having a diameter of from about 0.1 to about 0.5 microns is inserted directly into the nucleus of the cell. Through the bore of the micropipette exogenous material, such as DNA, is injected. An experienced, skilled technician can inject from about 500 to about 1000 cells per hour. Presently, however, micropipette microinjection requires some fairly sophisticated and expensive equipment, such as, a micropipette puller for making the needles, and a micromanipulator to position the needles correctly for injection. Moreover, extensive practice and training is needed for a technician to master this tedious technique. Micropipette microinjection is an effective method of gene transfer; however, because of the relatively small number of cells that may be transformed in any one experiment, the cost of the elaborate equipment necessary, and the level of skill needed to perform the procedure, microinjection using micropipettes is not a method of gene transfer available to the vast majority of researchers in the field.

Although a number of gene transfer techniques are available presently, no prior technique provides a safe, fast, effective, inexpensive, and reproducible method for genetically transforming a broad spectrum of living material regardless of cell, tissue or species type. Present methods are either expensive, slow, or yield results which are not reproducible. Moreover, some methods, such as the use of infectious agents, may even be hazardous to the researcher or the environment. Accordingly, a new apparatus and method for transforming cells, tissue, or species is needed.

BRIEF DESCRIPTION OF THE DRAWINGS

Advantages of the invention will become apparent upon reading the following detailed description and upon reference to the drawings in which.

DESCRIPTION OF THE PREFERRED EMBODIMENTS

The present invention is directed to an apparatus and methods for the introduction of exogenous materials, for example foreign DNA, into a variety of recipient cells. It is believed that the present invention should have a profound effect upon the variety of plants, and animals, that will become amenable to direct genetic manipulation.

The present invention uses aerosol beam technology to accelerate either wet or dry aerosol particles to speeds enabling the particles to penetrate living cells upon impact therewith. Aerosol particles suspended in a inert gas can be accelerated to a very high velocity during the jet expansion of the gas as it passes from a region of higher gas pressure to a region of lower gas pressure through a small orifice. This acceleration process has been well-studied and used for many years in the field of aerosol physics. The accelerated droplets may be positioned to impact a preferred target, for example, a plant or animal cell. When the particles include DNA or other macromolecules, the macromolecules are introduced into the cells. The droplets may be constructed as droplets of a sufficiently small size so that the cells survive the penetration. Once introduced into the target cell the macromolecules can elicit biological effects. This effect will depend on the specific properties of the macromolecules and the nature of the recipient cells. For example, DNA may be introduced into the target cell, thereby altering the genetic make-up of the cell. Because the method of introduction is a physical one, the biological barriers that restrict the application of other DNA transfer methods to a few plant species and a few cell types are not present. The size, kinetic energy and beam intensity of the aerosol stream can be precisely controlled over a wide range, and hence may be successful in penetrating and transforming a wide variety of cell types In addition, the use of a continuous aerosol beam will permit the treatment of a large number of cells in the course of any single treatment. Thus, the inventive method should be applicable to a wide range of plant species and cell types that have proved in the past to be quite impervious to standard methods of genetic engineering. According to a preferred embodiment, the apparatus and methods of the present invention are utilized to produce a transformed line of plants. Aerosol particles comprising exogenous genetic material are produced and accelerated to a speed enabling them to penetrate and enter into a living plant cell upon impact therewith. The cells are thereafter cultured to grow a plant. The progeny of the plant are subsequently screened using techniques well known to one skilled in the art of plant genetics, for transformed progeny.

Figure 3:
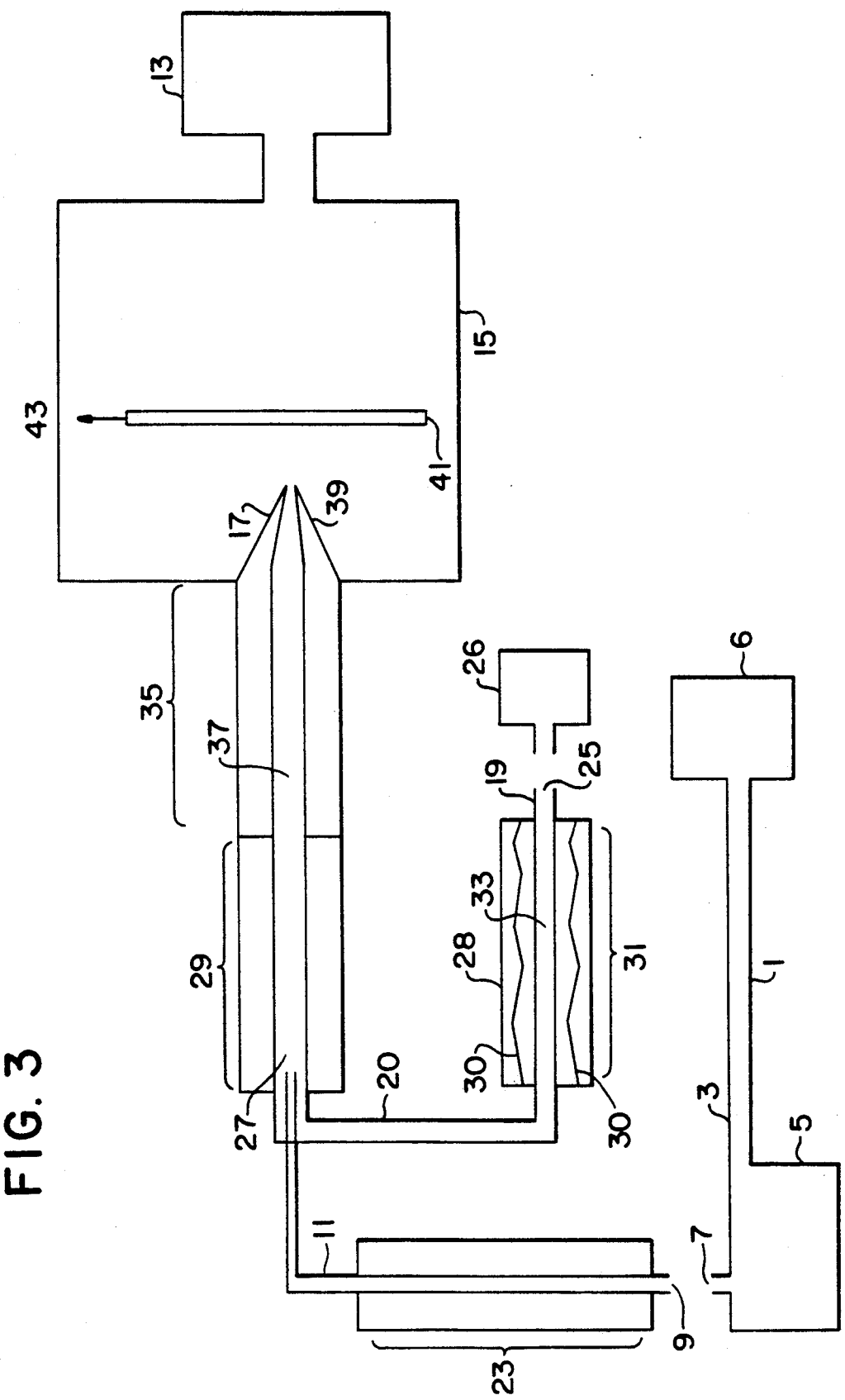
FIG. 3 is a schematic illustration of an aerosol beam microinjector additionally including means for adjusting the diameter of the injected droplet.

According to a preferred embodiment, the apparatus and methods of the present invention are utilized to produce transformed maize plants. Cells from an embryogenic culture of an alcohol dehydrogenese-deficient (adh−) recipient plant are preferably plated on an agar surface of osmotically supportive medium. They would then be placed in the chamber on the target positioning device for treatment with aerosol carrying a wild type adh gene on a plasmid. The apparatus shown in FIG. 3 is preferably used. The DNA plasmid would be adjusted to 3 mM $MgCL_2$ and rapidly mixed with 100% ethanol to yield 95% final ethanol concentration. The concentration of DNA would be such that each droplet of primary aerosol generated in the nebulizer contains an average of 2-3 plasmid molecules (about $10^{13}$ molecule per ml of final ethanol solutions). The primary aerosol, generated in the nebulizer would then be dried and the ethanol vapor trapped in the diffusion dryer. The DNA aerosol stream would be humidified with water $5 \times 10^{-16}$ g water vapor per primary aerosol particles, and the mixture cooled to 0° C. to generate aerosol droplets of relatively uniform size, preferably in the size range of 0.5-1.0 μm diameter. These would be accelerated by the expansion of the $N_2$ inert gas through a 250 mm orifice to strike the target cells 1.5 cm away from the orifice. The injected cells would then be cultured and tested by cytological staining for the presence of adh activity in the cells. An appropriate number of cells would be grown into plants and for the tested for the presence of the transforming DNA and for function of the adh gene.

A further preferred embodiment of the present invention utilizes the apparatus and methods of the present invention to effect genetic transformation of maize pollen. Pollen from a recipient variety deficient in adh would be plated on osmotically supportive agar medium and placed in the device shown in FIG. 3. Transforming DNA would be formed into a primary aerosol of 95% ethanol as described for embryogenic cell transformation, and then dried as set forth above. In this case, the aerosol stream would be humidified with perfluorocarbon vapor (3M or Air Products) at a density of $8 \times 10^{-12}$ g per primary aerosol droplet. Condensation at 0° C. would then generate 2 micron uniform diameter droplets. These would be accelerated with the inert gas expansion to impact the pollen grains. After 1 hr recovery period, the pollen would be transferred to silks of adh deficient corn plants. The seeds obtained would be planted and transformed plants recognized by the presence of adh-stainable pollen in samples from the mature plants.

Aerosol particles are formed by nebulizing solutions containing the macromolecule. Preferably, excess solvent is subsequently evaporated from the aerosol particles to reduce projectile size, thus increasing the rate of survival in the impacted target cells. When the aerosol particles are constructed as droplets the density of the final droplets is important, since less dense droplets may cause less damage to some target cells when they penetrate, while, on the other hand, more dense droplets may be required to penetrate certain target cells. Accordingly, the present invention provides means to modify both the size and density of the droplets as required for penetrating different cells. According to one preferred embodiment, the density of the droplets is from about 0.8 to about 8 gram/cc, and most preferably about 2 grams/cc. The density is modified by the addition of solutes, for example colloidal gold, to the solution prior to forming an aerosol or by using solvents, such as perfluorocarbons, that have different densities. Further, the apparatus of the present invention may be modified to include means for removing excess solvent, thus reducing droplet size, or adding additional solvent to the droplet, thus increasing the size of the droplet.

Figure 1:
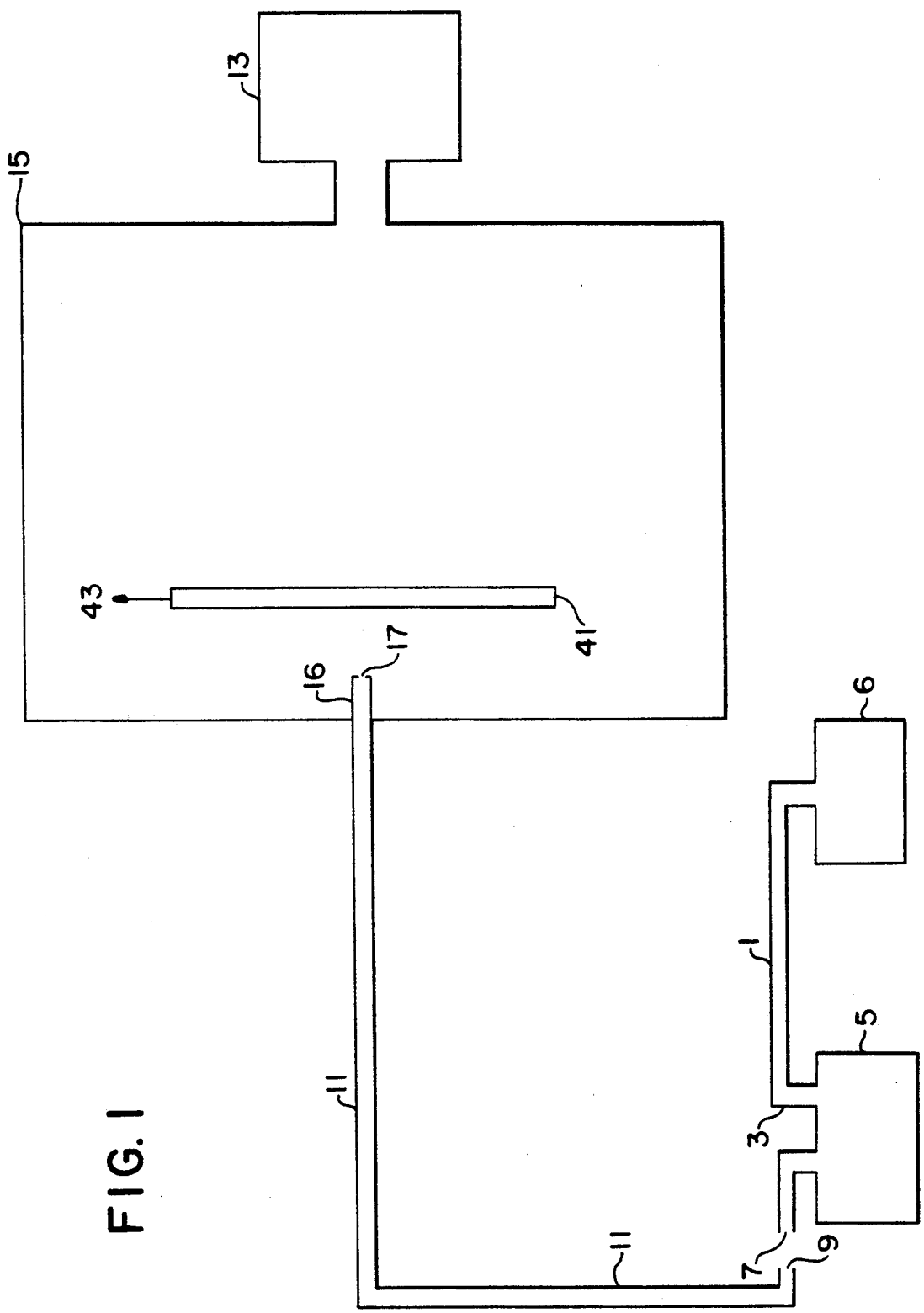
FIG. 1 is a schematic illustration of a aerosol beam microinjector.
Figure 2:
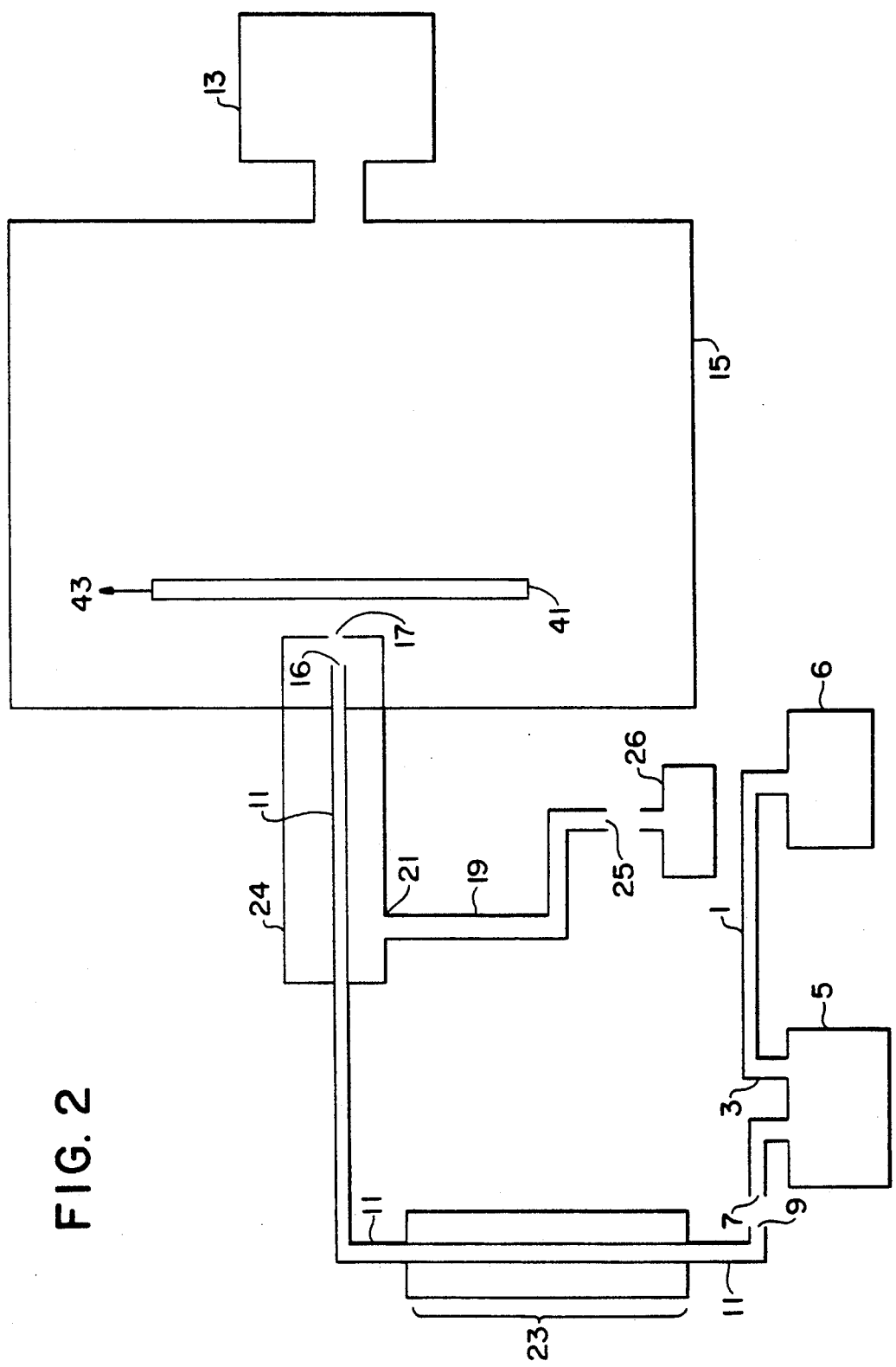
FIG. 2 is a schematic illustration of an aerosol beam microinjector including a drying tube and means for providing sheath flow.

FIGS. 1, 2 and 3, illustrate several embodiments of an aerosol beam microinjector of the present invention. Each Fig. will be discussed in detail when appropriate, otherwise the following discussion is applicable to each FIG. Compressed inert gas is filtered as it passes through a tubing 1 into the inlet 3 of a nebulizer 5 disbursing aerosol particles (a suspension of solvent and solute) into the inert gas to form an aerosol. The source of the compressed gas 6 preferably provides a gas pressure of from about 10 to about 100 psi at the inlet 3. However, the compressed gas most preferably provides about 30 psi at the inlet 3. Preferably, the projectiles (droplets of solvent and suspended particulate matter) have mass mean diameters of from about 0.1 to about 2 microns. The present inventor has determined that projectiles having diameters outside of this range are not preferable in the practice of the present invention. Projectiles having a diameter of greater than about 2 microns were found to cause an unacceptable level of cell death following impact, while projectiles having a diameter of below about 0.1 microns were unable to efficiently penetrate into the target cell.

The aerosol exits the nebulizer 5 through an outlet 7. The present inventor has determined that it is preferable to dissipate the pressure of the compressed gas prior to the acceleration of the aerosol. This is accomplished, in one preferred embodiment, by venting the aerosol to the outside atmosphere. As shown in FIG. 1, 2, and 3, the outlet 7 and the inlet 9 of tubing 11 do not abut each other, but are rather, positioned in a close proximity to each other. This arrangement allows the pressure of the compressed gas to dissipate, while further allowing the aerosol to enter inlet 9 of tubing 11. According to a further preferred embodiment not shown in the FIGS. the aerosol is discharged from the outlet 7 into a non-restrictive enclosure, such as a non-reactive plastic bag. Once the gas pressure from the compressed gas has been alleviated, a portion of the aerosol is drawn into the inlet 9 of a tubing 11. The aerosol is drawn into the tubing 11 by a negative or low gas pressure (a gas pressure below that of the surrounding atmosphere). This negative pressure is preferably about 1 atmosphere and is created within the tubing 11 by a high-volume vacuum pump 13 in communication with an air-tight vacuum housing 15 which is functionally connected to the outlet 16 of the tubing 11. If the aerosol is being discharged into the atmosphere, the inlet 9 of the tubing 11 is preferably positioned in a relatively close proximity to the nebulizer outlet 7. Preferably, this distance is about one-half inch.

Referring specifically to FIG. 1, FIG. 1 shows the tubing 11 entering the housing 15. FIG. 1 shows the tubing outlet 16 including a nozzle 17 through which the inert gas and the aerosol eventually passes through to reach the vacuum housing 15.

Returning, generally, to FIGS. 1, 2, and 3, the pressure within the tubing 11 and correspondingly within the vacuum housing 15 may be regulated by the pumping speed of the pump 13, the flow resistance caused by the nozzle 17, or the evaporation of solvent from samples within the vacuum housing 15. The aerosol is drawn through the length of tubing 11 to the nozzle 17. The nozzle 17 preferably has an aperture diameter of from 100 to 300 microns. The present inventor has determined that the most preferred aperture diameter of nozzle 17 is about 200 microns. The aerosol is thereafter drawn through nozzle 17 and into the vacuum housing 15.

The passage of the aerosol from the relatively high gas pressure area within tubing 11 into the relatively low gas pressure area within the vacuum housing 15 causes the inert gas to dramatically expand. The rapid expansion of the inert gas through the nozzle 17 causes the aerosol particles to accelerate. For example, when nitrogen is used as the inert gas, it has been determined that the aerosol particles can be accelerated up to speeds of from about 400 to about 800 meters/second. Further, if helium is used as the inert gas, the aerosol particles may be accelerated up to speeds of about 2000 meters/second. The vacuum housing 15 is continuously evacuated by the pump 13 to remove the inert gas and keep the pressure in the housing below the gas pressure in the tubing 11. According to one preferred embodiment, the gas pressure in housing 15 is from about 0.01 to about 0.05 atmospheres, and most preferably about 0.01 atmospheres.

When the inert gas is expanded and the aerosol is accelerated, an aerosol beam is generated. In the vacuum housing 15 the inert gas portion of the aerosol is expanded and removed and accelerated aerosol particles follow straight line trajectories. Aerosol beams are thus composed of accelerated isolated particles and droplets (hereinafter referred to as simply projectiles) moving on well defined, straight line trajectories at speeds up to 2000 meters/seconds.

Referring now to FIG. 2, FIG. 2 illustrates an aerosol beam microinjector including means for manipulating the size of the projectiles, and means for focusing the aerosol flow through the nozzle 17. As the aerosol is drawn through tubing 11 it is drawn into a drying tube 23. Drying tube 23 contains a desiccant which traps solvent evaporated from the surface of the solute, thus decreasing the diameter of the projectile. The flow rate of the aerosol, the length of the drying tube, the solvent used, and the desiccant contained in the drying tube, may all be modified to remove varying amounts of solvent from the aerosol. According to one preferred embodiment, the drying tube 23 has an internal diameter of about one-half inch and an effective length of about 60 cm. The drying tube 23 contains silica gel as a desiccant. The silica gel surrounds a central channel formed by a cylinder of 20 mesh stainless steel screen. Commercial drying tubes similar to the drying tube described above and useful in the practice of the present invention are available from TSI, Inc., Model 3062 Diffusion Dryer.

Once treated, the aerosol continues through tubing 11. The aerosol is discharged from outlet 7 of tubing 11 and into the precise center of a laminar flow of dry, filtered inert gas. The aerosol is thus entrained in the center of a gas stream moving up to and through the nozzle 17. This is preferable because it increases the average velocity of the projectiles, focuses the aerosol beam, and prevents nozzle clogging. When a gas flows through a nozzle 17, the velocity profile is never constant over the entire cross section. The particles nearest the nozzle wall will have velocities substantially less than particles traveling in the center of the beam. Further, the radial expansion of the carrier gas will cause the aerosol beam to expand radially outward. Particles near the beam center are not influenced by this radial expansion but particles at increasing radii obtain an increasing radial velocity component. Accordingly, FIG. 2 illustrates an aerosol beam microinjector which includes means for reducing the radial expansion of the aerosol beam and maintaining a substantially uniform velocity through the cross section of the beam.

FIG. 2 shows a piping 19 drawing filtered inert gas into its length and transporting that gas to the inlet 21 of the sheath flow piping 24. The inert gas, which accounts for the sheath flow, enters the piping 19 with no positive pressure and is drawn from a non-restrictive reservoir of inert gas or from the outside atmosphere when the inert gas is released from a source 26 in the immediate area of the inlet 25 of piping 19, as shown in FIG. 2. The aerosol is discharged from tubing 11 into the center of the sheath flow piping 24. The aerosol is entrained in the laminar flow of the inert gas in the sheath flow piping 24. The laminar flow focuses the aerosol through the center of the nozzle 17, thus allowing the aerosol to maintain a substantially uniform velocity across its cross section. The laminar flow also reduces beam spreading so that a more focused beam is obtained. According to one preferred embodiment the laminar flow accounts for 50% of the flow through the nozzle 17. Referring to FIG. 3, FIG. 3 illustrates an aerosol beam microinjector having additional means to control particle size. As in the apparatus illustrated in FIG. 2, the apparatus of FIG. 3 includes a drying tube 23. However, in the apparatus of FIG. 3 the drying tube removes substantially all the solvent from the aerosol. Thus, the aerosol exiting the drying tube 23 through the tubing 11 is comprised substantially of dry solute. The solute is discharged from the tubing 11 into a channel 27 of a gas reheater 29. In addition to the dry solute solvent, solvent saturated carrier gas is discharged into the channel 27.

The solvent saturated inert gas is produced in the vapor satuator 31 and is transported through the piping 19 to the channel 27 of the reheater 29. Filtered dry inert gas is draws from a source 26 into the piping 19, as discussed for the apparatus of FIG. 2. The inert gas thereafter enters the vapor saturator 31, wherein solvent vapor is added to the inert gas to the point of saturation. The vapor saturator 31 is preferably constructed to contain solvent moistened fibrous material forming a central channel 33. Surrounding the solvent-moistened material is preferably an aluminum block 28 heated to a desired temperature with resistive heaters 30. Preferably, this temperature is from about 500° to about 100° C. The heat causes the solvent moistened material to release solvent vapor which is entrained by the inert gas. Although this is a preferred construction for the vapor saturator 31, other means to saturate the inert gas with solvent vapor may be utilized in the practice of the present invention.

The solvent-saturated inert gas is discharged from the vapor saturator 31 into piping 20 which communicates with channel 27 of the reheater 29. The dry aerosol is discharged from tubing 11 also into the reheater 29. The reheater 29 heats the dry aerosol and the solvent-saturated inert gas to a constant temperature. This facilitates the diffusion and mixing of the vapor-saturated inert gas and the dry aerosol particles. Preferably, the resulting mixture is heated to about 50° C.

From the channel 27 of the reheater 29 the solvent-saturated inert gas and the dry aerosol particles move to a vapor condenser 35. The vapor condenser 35 is preferably constructed as having a central channel 37 wherein by reducing the temperature, the solvent vapor is condensed onto the aerosol particles. Depending on the temperature within the channel 37, the amount of solvent condensed may be controlled. Thus, the projectile size may be precisely controlled. According to one embodiment, the vapor condenser 35 includes Lapeltier Coolers, obtained from Marlow Industries. The vapor condenser outlet 39 includes the nozzle 17, and is positioned within the vacuum housing 15.

Referring again to FIGS. 1, 2, and 3, placed in the path of these projectiles is the target support platform 41. The target support platform 41 is a substantially horizontal surface capable of supporting target cells thereon and being preferably moveable along the X, Y and Z axis. According to the most preferred embodiment, the target support platform 41 is provided with, supported by, and affixed to a motorized positioning member which enables it to be positioned either closer or farther away from the nozzle 17. Through experimentation, the inventor has determined that the target support platform 41 is preferably positioned about 1.5 cm from the nozzle 17. However, this distance may be varied depending on the specific application. For example, it has been determined that the greater the distance the target support platform 41 is from the nozzle 17 the slower the impact speed of the projectiles. This is due to the background pressure in the vacuum housing 15 reducing the speed of the projectiles as they travel through the housing 15. According to the most preferred embodiment, the target support platform 41 is rotated and is moved by the positioning member along one linear axis 43. This allows for a biological sample placed on the target support platform 41 to be impacted throughout its entirety by projectiles. The present inventors had determined that an effective rate of rotation about axis 43 is 40 rpm and that an effective rate of simultaneous linear advance along axis 43 is 333 microns per revolution. This allows the entirety of a biological sample of approximately 5×7 centimeters to be impacted (hereinafter referred to as scanned) in three to four minutes.

Preferable inert gases utilized in the practice of the present invention are filtered compressed inert gas. A preferable carrier gas useful in the practice present invention is one gas selected from the group of gases consisting of carbon dioxide, room air, hydrogen, helium, and nitrogen. However, it should be noted, that any compressed gas substantially nontoxic to living materials may be utilized in a practice of the present invention. The source of the carrier gas 6 is a source of gas capable of generating a gas pressure of 30 pounds per square inch at the inlet 3 of the nebulizer 7. Preferred sources of Compressed gas are compressed gas cylinder, and laboratory electrolytic cell gas generators.

The nebulizer 5 utilized in the practice of the present invention may be any nebulizer 5 which produces aerosols having droplet sizes of from 0.1 to about 3 microns in diameter. Although ultrasonic nebulizers, such as the LKB Instruments, model 108 may be used in the practice of the present invention, down draft or respiratory inhalation nebulizers of the Lovelace design are most preferred. The most preferred nebulizers of the present invention is a nebulizer used in inhalation therapy obtained from Inhalation Plastic, Inc., model 4207, of the Lovelace design. These nebulizers are single use, disposable units that generate aerosol droplets with median mass diameters in the range of two microns. They require only a few millimeters of solution to operate efficiently and generate dense mist having up to $10^{10}$ droplets per liter of gas.

EXAMPLES

Examples 1-3 are presented to demonstrate the optimal range of particle sizes effective in transforming target cell in the practice of the present invention.

Examples 4-8 are presented to demonstrate the successful transformation of *Chlamydomonas reinhardtii* cells using the apparatus and methods of the present invention.

EXAMPLE 1

Aerosol Beam Microinjection of Carboxyfluorescein into *Chlamydomonas reinhardtii* using 2 micron mass median diameter solute/solvent droplets

*Chlamydomonas reinhardtii* is a unicellular eucaryotic green alga. Cells of the wild type strain of *Chlamydomonas reinhardtii* (Chlamydomonas) were used as the target cells. The cells were cultured in tris-acetate-phosphate (TAP) liquid medium. (Harris, E. H. *Chlamydomonas Source Book*, Academic Press, 1989). The cells were concentrated by centrifugation and resuspended in TAP at a concentration of 10 cells/ml. 100 microliters of the cell suspension were subsequently plated onto an agar medium slab containing TAP and 1.5% by weight agar for consistency. The slab also included an inert layer of Miracloth (Calbiochem, Col.) which was washed and steam autoclaved. Miracloth was included to facilitate the handling of the agar slabs. The slabs were thereafter incubated at 25° C. for from 1 to about 4 hours. Following the incubation period the slabs were chilled at 4° C. for about an hour.

The schematic of the apparatus used in the instant example is shown in FIG. 1. The aerosol was produced by a respiratory therapy nebulizer, model 4207 obtained from Inhalation Plastic, Inc. The mass median diameter of the aerosol droplets produced by the nebulizer was 2 micrometers, according to manufacturer's literature. The nebulizing solution used was a buffered aqueous solution containing 0.01M sodium phosphate Ph 7.0 and 10 mg/ml of carboxyfluorescein. Both chemicals were obtained from the Sigma Chemical Company. The carrying gas was compressed nitrogen having a flow rate of 4 liters/min to achieve 30 psi in the nebulizer. The positive pressure created by the carrier gas was neutralized by opening the output piping of the nebulizer to the outside atmosphere The piping leading to the vacuum housing (tubing 11 in FIG. 1) was positioned in close proximity to the open outlet piping of the nebulizer. The negative pressure in the system was created by a high-volume vacuum pump attached to the vacuum chamber. The vacuum pump used was a Marvac model R-10, set at 170 liters/min. The aerosol was accelerated into the vacuum housing through a nozzle having a diameter of 200 microns. The agar slab on which the cells were plated was placed on the target support platform, which, in turn, was positioned 1.5 cm from the nozzle. The target support platform was rotated at 40 rpm, and advanced at a rate of 333 micrometers/revolution. The entire slab was scanned (impacted by carrier gas or droplets) in about 3 to 4 minutes. A control group of cells (non-impacted cells) was created on the slab by interrupting the aerosol flow in a regular pattern. Thus, the control cells on the slab are impacted with only carrier gas.

To determine the morphology of the cells impacted, the scanned slab was examined using a 40×dissection microscope. To determine the pattern of carboxyfluorescein impact, the slab was examined using a UV Products model T-33 longwave UV transilluminator. To determine cell survival after impact, the slab was placed on a petri dish containing TAP medium and incubated for 2 days. To determine if microinjection of carboxyfluorescein had occurred in the impacted cells, the cells were removed from the slab, washed, resuspended in TAP liquid medium, and examined with a Nikon Labophot epifluorescence microscope, using a UV filter cube to observe carboxyfluorescein fluorescence.

RESULTS

Following scanning the slab with 2 micron droplets no intact cells were observed in the impact areas. Fluorescence was observed uniformly in all the impact areas. There was no growth in the impact area following a two day incubation. Thus, it was determined that cells impacted by droplets having a mass median diameter of 2 microns or greater would not survive the procedure.

EXAMPLE 2

Aerosol Beam Microinjection of Carboxyfluorescein into *Chlamydomonas reinhardtii* using 0.1 micron mass median diameter solute/solvent droplets The protocol set forth in Example 1 was followed in Example 2 with the following exception. A drying tube was included in the apparatus. The drying tube was located in close proximity to the nebulizer, as shown in FIG. 2. The drying tube had an internal diameter of ½ inch and was 60 cm long. It contained silica gel which surrounded a central channel formed by a cylinder of 20 mesh stainless steel screening. The drying tube of the instant example was prepared by the inventor; however, similar drying tubes are available from TSI, Inc. (model 3062 Diffusion Dryer). The solvent was completely removed by the drying tube so that only a dry aerosol of the solutes remained to be accelerated an impact the cells. Based on the mean masses of the solutes it is estimated that the impacting projectiles had a mass median diameter of about 0.1 microns.

RESULTS

Following scanning the slab with 0.1 micron projectiles, visual examination with the 40×dissection microscope revealed that all the cells in the impacted area were intact. Further, the distribution of carboxyfluorescein on the slab was uniform throughout the impact areas. Thus, demonstrating that the cells has been impacted. There was 100% cell survival after a 2 day incubation. However, no fluorescence was observed in the washed and resuspended impacted cells. This suggested that no carboxyfluorescein was successfully injected into the cells.

EXAMPLE 3

Aerosol Beam Microinjection of Carboxyfluorescein into *Chlamydomonas reinhardtii* on sorbitol containing medium using 2.0 micron mass median diameter solute/solvent droplets Example 3 followed the protocol set forth in Example 1 with the following exceptions: the agar slab included 0.5M sorbitol to help osmotically stabilize the impacted cells; and the cells were immediately washed and resuspended following microscopic and UV inspection of the slab. Thus, the incubation step, which determined cell survival was postponed until it was determined if carboxyfluorescein had been successfully microinjected into the cells.

RESULTS

Following scanning the slab with 2 micron droplets the cells were inspected with the 40×dissection microscope and substantially all the cells in the impact area appeared intact. Following washing and resuspension, substantially all of the impacted cells contained florescent carboxyfluorescein. Thus, carboxyfluorescein was successfully microinjected into the cells. However, following subsequent replating of the impacted cells, NO cell survival was below 0.1%.

EXAMPLE 4

Transformation of *Chlamydomonas reinhardtii* Mutant D15 through the microinjection of DNA plasmid p71.

The target cells were wild type *Chlamydomonas reinhardtii* mutated (Mutant D15) to be incapable of growing on minimal media because of a deletion of the chloroplast tscA gene that renders them defective in photosynthesis. No spontaneous reversion of this deletion has been observed. The DNA plasmid p71 used as the genetic transforming agent carries the *Chlamydomonas reinhardtii* chloroplast DNA fragment Eco18 (Harris, E. H. *Chlamydomonas Source Book*, Academic Press, 1989) cloned in *E. coli* in the pUC8 cloning vector. It was obtained from Dr. Jane Aldrich, BP America. This fragment has the intact tscA gene that was deleted from the D15 mutant chloroplast DNA.

The nebulizing solution included 10 mM tris-Cl pH 8.0, 1 mM disodium EDTA, 3 mM magnesium chloride, 0.1 mg/ml plasmid p71, 10% polyethylene glycol 6000, and distilled water. All reagents were obtained from the Sigma Chemical Company. Polyethylene glycol and magnesium chloride are included in the solvent mixture to cause the tight condensation of the DNA, which protects it from shear degradation during aerosol formation. The effectiveness of this treatment was verified in preliminary experiments in which the aerosol generated from this solvent was recovered and the DNA analyzed by electrophoresis for intactness. In addition, it was tested for biological function by transformation of *E. coli*. The target cells were grown in TAP liquid medium and concentrated by centrifugation. The cells were plated on an agar slab and incubated as described in Example 1. Before scanning, the agar slab was placed onto a petri plate containing solidified TAP medium containing 0.5M sorbitol for two hours at room temperature and for an additional one hour at 4° C. It is believed that the presence of the sorbitol in the medium helps the cells to maintain their integrity during an osmotically sensitive period during recovery after being impacted by the projectiles.

The apparatus used in Example 4 is illustrated schematically in FIG. 2. The drying tube utilized was the same drying tube as used in Example 2. The laminar flow accounted for 50% of the total flow through the nozzle. The nozzle was 200 microns in diameter. The target cells were positioned 1.5 cm from the nozzle and the procedure used for scanning the surface of the agar slab was the same as was used in Examples 1–3. The carrier gas was nitrogen and the flow rate through the drying tube was set at 160 ml/minute.

Following the scanning of the surface of the agar slab, the impacted cells were screened for the presence of transformants. The slab was transferred to tris-minimal medium (Harris, E. H., *Chlamydomonas Source Book*, Academic Press, 1989) and incubated in light. Thus, only those cells which had been transformed could photosynthesize in the presence of light and survive. Following incubation for two days, two colonies were observed on the minimal medium. These colonies were removed and streaked onto petri dishes containing tris-minimal medium. Subsequently, a plurality of colonies grew. This growth test was repeated a second time after seven days.

Total cell DNA was isolated from the transformed *Chlamydomonas reinhardtii* cells. The cells were grown to a concentration of $3 \times 10^6$ cells/ml in TAP liquid medium. They were harvested by centrifugation at 5000 Xg for five minutes and resuspended to a final concentration of $10^8$ cells per ml in ice water buffer I (10 mM sodium chloride, 10 mM tris-Cl, 10 mM sodium EDTA, pH 8.0). This suspension was incubated with an equal volume of ice cold 4M lithium chloride and incubated for thirty minutes. The cells were then harvested by centrifugation as before and then washed twice with ice cold buffer I. The cell pellet obtained in the final wash was weighed and then the cells resuspended in 10 ml per gram pellet of ice cold buffer I. One third volume of 10% (w-v) sodium dodecyl sulfate detergent was added along with 0.1 mg/ml of Pronase (Sigma). This mixture was incubated at 37° C. for three hours or longer until the chlorophyll was entirely converted to pheophytin (olive-green in color). This solution was then cooled to room temperature and extracted twice with freshly distilled phenol (the phenol was distilled, washed with one half volume of 0.5M tris base and equilibrated before use with one volume of 10 mM tris-Cl pH 8.0, 1 mM disodium EDTA, 50 mM sodium chloride ). The aqueous phase separated from the second phenol extraction was mixed with one half volume of 7.5M ammonium acetate and then centrifuged in a micro centrifuge (Eppendorf) for one minute. The supernatant was thereafter mixed with two volumes of ethanol and placed in −70° C. freezer for ten minutes. The precipitated nucleic acids were collected by centrifugation in the micro centrifuge for one minute and the supernatant discarded The pellet was resuspended in one tenth of TE buffer (10 mM tris-Cl, 1 mM disodium EDTA, pH 8.0). This ammonium acetate precipitation step was repeated once more.

The DNA obtained from the transformants was thereafter analyzed. One aliquot of the DNA obtained as set forth above from one of transformants was digested with restriction enzyme EcoRI, one with a combination of BamHI and BglII and one with SmaI, using the enzymes according the manufacturer's instructions (Boehringer-Mannheim). A similar digestion was performed on DNA from wild-type cells, DNA from the D15 mutant cells, and DNA from the p71 plasmid used in the transformation experiment. The DNA fragments were separated by electrophoresis in 0.7% agarose gels using tris-borate-EDTA buffer according to standard procedures. The DNA was transferred to Nytran membranes (Schleicher and Schuell) using the standard Southern blot procedure. DNA for use as probes to detect specific fragments on the membrane was radioactively labeled by random priming, using a kit according to the manufacturer's instructions (Boehringer-Mannheim). Probes were prepared from pUC18 plasmid DNA and from fragments of the Eco-18 chloroplast DNA isolated from the p71 plasmid.

The hybridization with the pUC probe reveals the presence of an intact pUC vector sequence in transformants. No reactivity was seen in the wild type or D15 strain DNA samples. These results demonstrate that the DNA was microinjected into the target mutant cells to produce transformants in the experiment.

While the invention is susceptible to various modifications and alternative forms, specific embodiments thereof have been shown by way of example in the drawings and have been described in detail It should be understood, however, that it is not intended to limit the invention to the particular forms disclosed, but on the contrary, the intention is to cover all modifications, equivalents, and alternatives falling within the spirit and scope of the invention as defined by the appended claims.

I claim:

1. A method of introducing nucleic acids into a living cell, the method comprising the steps of:
   a) producing aerosol droplets comprising said nucleic acids;
   b) adjusting the diameter of the droplets by drying them; then
   c) accelerating said droplets to a speed enabling them to penetrate and enter into said cell upon impact therewith; and
   d) impacting said living cell with said accelerated aerosol droplets.

2. The method of claim 1 wherein said nucleic acids are DNA.

3. A method of introducing exogenous DNA into a living cell, the method including the steps of:
   a) solubilizing said exogenous DNA to form a solution;
   b) producing aerosol droplets from said solution;
   c) adjusting the diameter of the droplets by drying the droplets to a diameter of a size range from above 0.1 to below 20 microns; and
   d) accelerating said droplets to a speed enabling said droplets to penetrate and enter into said living cell upon impact therewith, said droplets being accelerated by passing from an area of high gas pressure through an aperture having a diameter of about 100 to 300 microns and into an area of low gas pressure, said area of low gas pressure having an atmospheric pressure of about 0.01 atmospheres and said area of high gas pressure having an atmospheric pressure of about 1 atmosphere, said living cell being positioned in said area of low gas pressure such that it is impacted by a plurality of the accelerated droplets; and
   e) impacting said living cell with said accelerated droplets, said droplets penetrating and entering into said cell.

4. The method of claim 3 wherein the cell is a plant cell.

5. A method of introducing a nucleic acid into a living cell, the method comprising:
   a) producing aerosol droplets comprising said nucleic acid;
   b) subjecting said droplets to a pressure differential such that said droplets are accelerated to a supersonic speed enabling them to penetrate and enter said cell upon impact therewith; and
   c) impacting said living cell with said accelerated droplets.

6. The method of claim 5 wherein the pressure differential ranges from ambient pressure to a substantial vacuum.

7. The method of claim 6 wherein the ambient pressure is about 1 atm and the substantial vacuum is about 0.01 atm.

8. The method of claim 5 wherein the nucleic acid is DNA.